United States Patent [19]

Iguchi et al.

[11] Patent Number: 5,612,390
[45] Date of Patent: Mar. 18, 1997

[54] THIOL METHACRYLATE OR ACRYLATE RESIN AND A METHOD OF MAKING SAME

[75] Inventors: Yuichiro Iguchi; Michio Kimura, both of Otsu; Koichiro Oka, Ibaraki, all of Japan

[73] Assignee: Toray Industries, Inc., Japan

[21] Appl. No.: 480,090

[22] Filed: Jun. 7, 1995

Related U.S. Application Data

[62] Division of Ser. No. 351,687, Dec. 8, 1994, Pat. No. 5,502,141, which is a division of Ser. No. 169,603, Dec. 17, 1993, Pat. No. 5,399,735, which is a division of Ser. No. 1,075, Jan. 6, 1993, Pat. No. 5,294,690, which is a continuation of Ser. No. 844,477, Mar. 2, 1992, Pat. No. 5,247,041, which is a continuation of Ser. No. 482,285, Feb. 20, 1990, abandoned.

[30] Foreign Application Priority Data

Feb. 22, 1989 [JP] Japan ..................... 1-42822
Apr. 18, 1989 [JP] Japan ..................... 1-98372

[51] Int. Cl.$^6$ ..................................... C08F 2/48
[52] U.S. Cl. ........................... 522/173; 522/180
[58] Field of Search ..................... 522/173, 180; 526/289

[56] References Cited

U.S. PATENT DOCUMENTS 4,931,521  6/1990  Matsuda et al. ................ 526/286

FOREIGN PATENT DOCUMENTS

63-316766  12/1988  Japan .
3-11054    1/1991   Japan .

Primary Examiner—Christopher Henderson
Attorney, Agent, or Firm—Austin R. Miller

[57] ABSTRACT

A thiol methacrylate or acrylate compound represented by the formula (1) or (2),

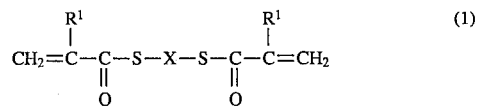

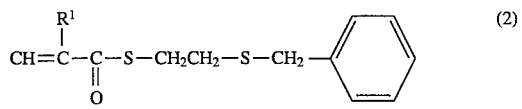

wherein $R^1$ is H or $CH_3$ and X is selected from:

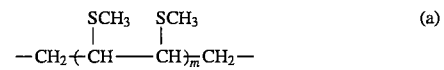

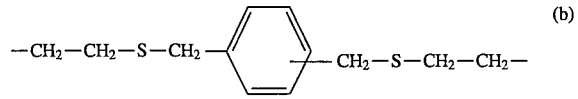

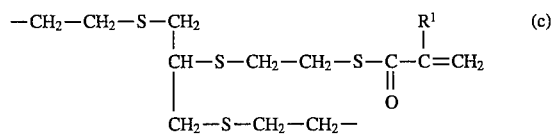

wherein $R^1$ is H or $CH_3$ and m is an integer of 1 to 4. The thiol methacrylate or acrylate compound gives a resin having a high refractive index, a large Abbe number, and a good hardness and heat resistance, and giving little or no smell at processing.

9 Claims, 3 Drawing Sheets

THIOL METHACRYLATE OR ACRYLATE RESIN AND A METHOD OF MAKING SAME

This application is a division of application Ser. No. 08/351,687, filed on Dec. 8, 1994, now U.S. Pat. No. 5,502,141, which is a division of application Ser. No. 08/169,603, filed on Dec. 17, 1993, now U.S. Pat. No. 5,399,735, which is a division of application Ser. No. 08/001,075, filed on Jan. 6, 1993, now U.S. Pat. No. 5,294,690, which is a continuation of prior application Ser. No. 07/844,477 filed on Mar. 2, 1992, now U.S. Pat. No. 5,247,041, which is a continuation of prior application Ser. No. 07,482,285 filed Feb. 20, 1990, now abandoned.

BACKGROUND OF THE INVENTION

1. Field of the Invention

The present invention relates to a novel thiol (meth)acrylate, a resin formed from this (meth)acrylate and a high-refractive-index plastic lens composed of this resin.

2. Description of the Related Art

Olefinic thermosetting resins generality have an excellent heat resistance and chemical resistance, and especially, a resin composed of diallyl phthalate is widely used on an industrial scale because of its excellent heat resistance and chemical resistance and good dimensional stability. In some application fields, higher dimensional stability or chemical resistance and reduced water-absorbing characteristics, however, are required.

Diethylene glycol bisallyl carbonate is often applied to optical uses. However, the diethylene glycol bisallyl carbonate used for optical articles has a problem in that the refractive index is low.

For eliminating this disadvantage, there have been proposed thiol (meth)acrylates, for example, resins composed mainly of an aromatic thiol ester (Japanese Unexamined Patent Publication No. 63-316766), and an aliphatic thiol ester (U.S. Pat. No. 4,810,812) and Japanese Unexamined Patent Publication No. 63-188660).

Resins proposed in Japanese Unexamined Patent Publication No. 63-316766, U.S. Pat. No. 4,810,812, and Japanese Unexamined Patent Publication No. 63-188660 still have a problem in that optical characteristics having a good balance between a high refractive index and a large Abbe number cannot be obtained. Furthermore, these resins emit a strong offensive smell at the time of processing such as cutting or polishing. Moreover, since these resins are solid at normal temperature, cast polymerization cannot be performed at normal temperature, and the resins have a poor hardness and heat resistance.

SUMMARY OF THE INVENTION

The present invention solves the above-mentioned problems of conventional techniques, and a primary object of the present invention to provide a thiol (meth)acrylate valuable as a monomer for the production of a resin which has a high refractive index and a large Abbe number, gives little or no smell at processing and has excellent hardness and heat resistance; a resin composed of this monomer; and a high-refractive-index lens formed of this resin.

In accordance with the present invention, there is provided a thiol methacrylate or acrylate compound represented by the following formula (1) or (2):

wherein $R^1$ represents a hydrogen atom or a methyl group and X represents a divalent group selected from the group consisting of:

wherein $R^1$ is the same as defined above and m is an integer of from 1 to 4.

The present invention further provides a thiol methacrylate or acrylate resin prepared by polymerizing the thiol methacrylate or acrylate compound of the formula (1) or (2) or a monomer mixture comprising at least 10% by weight of at least one of the thiol methacrylate or acrylate compounds of the formula (1) or (2).

The present invention further provides a high-refractive-index plastic lens composed of the above-mentioned thiol methacrylate or acrylate resin.

DESCRIPTION OF THE PREFERRED EMBODIMENTS

The compound of the present invention represented by the formula (1) wherein X is the divalent group of the formula (a) can be synthesized by reacting a divalent mercaptan compound (D), synthesized through a synthesis scheme passing through compounds represented by the following formulae (A) through (C), with a (meth)acrylic acid halide in the presence of an alkali such as a metal hydroxide or a tertiary amine:

(A)

(B)

-continued (C)

(D)

The compound of the present invention, represented by the formula (1) wherein X is the divalent group of the formula (b) can be synthesized by reacting a mercaptan compound (G), synthesized through a synthesis scheme passing through compounds represented by the following formulae (E) and (F), with a (meth)acrylic acid halide in the presence of an alkali such as a metal hydroxide or a tertiary amine:

The compound of the present invention, represented by the formula (1) wherein X is the divalent group of the formula (c) can be synthesized by reacting a trivalent mercaptan compound (J), synthesized through a synthesis scheme passing through compounds represented by the following formulae (H) and (I), with a (meth)acrylic acid halide in the presence of an alkali such as a metal hydroxide or a tertiary amine The compound of the present invention represented by formula (2) can be synthesized in a manner similar to the compound of the formula (1) wherein X is the divalent radical of the formula (b), except that a mercaptan compound (M) is synthesized through a synthesis scheme passing through compounds represented by the following formulae (K) and (L), and is then reacted with a (meth)acrylic acid halide.

(K)

(L)

(M)

Especially, if a tertiary amine in an amount of 3 to 95 molar equivalents to the —SH group and a metal hydroxide in an amount of 5 to 120 molar equivalents to the –SH group are used in combination as the dehydrochlorinating agent for forming the thiol (meth)acrylate monomer, the purity and yield of the monomer can be increased.

A resin having an excellent transparency can be prepared by incorporating 0.001 to 5 parts by weight of a radical polymerization initiator such as a peroxide or azo type initiator customarily used for the radical polymerization in 100 parts by weight of the thiol (meth)acrylate monomer or a monomer mixture comprising at least 10% by weight of the thiol (meth)acrylate monomer and polymerizing the monomer or monomer mixture by application of heat or irradiation with light. In this case, a monomer other than the thiol (meth)acrylate of the present invention can be copolymerized with the thiol (meth)acrylate.

In this copolymerization, in view of the characteristics of the obtained resin, at least one monomer selected from the group consisting of monomers represented by the formulae (1) and (2) according to the present invention is preferably used in an amount of at least 10% by weight.

Olefinic compounds can be used as the comonomer to be added without any particular limitation. (Meth)acrylic compounds, styrene compounds, acrylonitrile and N-phenylmaleimide are preferably used. As specific examples, there can be mentioned methyl (meth)acrylate, ethyl (meth)acrylate, propyl (meth)acrylate, benzyl (meth)acrylate, phenyl (meth- )acrylate, cyclohexyl (meth)acrylate, cyclohexylmethylene (meth)acrylate, styrene, vinylnaphthalene, halogen-substituted styrene, α-methylstyrene, divinylbenzene, diallyl phthalate, ethylene glycol di (meth)acrylate, bisphenol A di(meth)acrylate, bisphenol A di[hydroxyethyl (meth)acrylate], tetrabromobisphenol A di(meth)acrylate, tetrabromobisphenol A di[hydroxyethyl (meth)acrylate], triallyl lsocyanurate, pentaerythritol tetrakis(meth)acrylate, diethylene glycol bisallyl carbonate, and compounds represented by the following formula (N):

wherein $R^2$ represents a hydrogen atom or a methyl group.

The compound represented by the formula (N) can be synthesized by reacting a dithiol represented by the following formula (O):

with (meth)acrylic acid chloride in the presence of an alkali such as a metal hydroxide or a tertiary amine.

When the compound represented by the formula (N) is homopolymerized, a resin having a refractive index of 1.69 is obtained, and the specific gravity of the resin is as low as 1.23. Since the resin is solid at normal temperature, when a polymer is obtained by the cast polymerization, copolymerization with another monomer is carried out, whereby a polymer having well-balanced optical characteristics can be obtained.

If a polyfunctional thiol compound is added as the copolymerization component in addition to the above-mentioned olefinic compound, a resin having an excellent processability can be obtained. As the polyfunctional thiol compound, there can be mentioned pentaerythritol tetrakisthioglycolate, trtsmercaptopropyl isocyanurate, and compounds represented by the above-mentioned formulae (D), (G), (J) and (O).

To obtain a resin having excellent mechanical characteristics, preferably a monomer mixture comprising 15 to 90% by weight of the thiol (meth)acrylate of the formula (1) or (2) and 10 to 85% by weight of styrene can be copolymerized. In this case, up to 75% by weight of another olefinic compound as mentioned above except for the thiol (meth)acrylate and styrene can be further copolymerized. A halogen-containing or halogen-free di(meth)acrylate having bisphenol A in the molecule structure can be preferably used as the olefinic compound.

As the di(meth)acrylate having bisphenol A in the molecule structure, there can be mentioned, for example, compounds represented by the following formula:

wherein $R^3$ represents a hydrogen atom or a methyl group.

Various thiol (meth)acrylate monomers represented by the formulae (1) and (2) can be used for the production of the above-mentioned copolymer without any limitation, and there can be obtained resins having not only excellent mechanical properties but also excellent optical characteristics such as a high refractive index and a large Abbe number.

To obtain a resin having excellent abrasion characteristics, preferably 15 to 90% by weight of at least one thiol (meth)acrylate monomer of the formula (1) or (2) is copolymerized with 10 to 85% by weight of a monomer having both of a urethane bond and a (meth)acryl group in the molecule. In this case, up to 75% by weight of another copolymerizable olefinic compound as mentioned above (except for the thiol (meth)acrylate and the monomer having both of a urethane bond and a methacryl or acryl group in the molecule) can be further copolymerized.

As the monomer having both a urethane bond and a (meth)acryl group in the molecule, there can be mentioned, for example, monomers having a substituent represented by the following formula:

wherein Y represents an alkylene group having 1 to 10 carbon atoms, $R_4$ represents a hydrogen atom or a methyl group, and l is an integer of from 0 to 3.

The kind of the thiol (meth)acrylate of the formula (1) or (2) is not particularly critical, and there can be obtained resins having not only excellent abrasion characteristics but also excellent optical characteristics such as a high refractive index and a large Abbe number.

The cast polymerization is preferably adopted for preparing a resin from the thiol (meth)acrylate of the present invention. As a preferred example of the cast polymerization process, there can be mentioned a process comprising casting the thiol (meth)acrylate of the present invention or a liquid mixture of the thiol (meth)acrylate with at least one monomer selected from the above-mentioned copolymerizable monomers, together with a polymerization initiator, into a mold assembly composed of a glass mold or metal mold and an adhesive tape or a plastic gasket, and effecting the polymerization by heating at 30° to 150° C. for 0.1 to 40 hours or by irradiation with ultraviolet rays.

In the preparation of a resin from the thiol (meth)acrylate, the polymerization is preferably effected by using a peroxide initiator such as benzoyl peroxide, t-butyl peroxyisobutyrate, diisopropyl peroxydicarbonate or t-butyl peroxypivalate, whereby a lens having an excellent appearance can be obtained.

By using the thiol (meth)acrylate of the present invention, a resin having a high refractive index, a large Abbe number and an excellent transparency can be obtained. Furthermore, although the obtained resin is a sulfur-containing resin, no smell is generated at processing. Moreover, since the thiol (meth)acrylate is a thioester compound, the obtained resin have a lower water absorption and a higher chemical resistance than those of resins derived from ester compounds.

Moreover, if a hard coat film or a reflection-preventing film is formed on the surface of the obtained resin, an article having a high surface hardness or an excellent light-transmitting property can be obtained. When the hard coat film or reflection-preventing film is formed, the surface of the resin substrate can be subjected to a preliminary treatment such as an alkali treatment or a plasma treatment, whereby the adhesion between the resin substrate and the hard coat film or reflection-preventing film can be improved. As the hard coat film, there can be mentioned an organic film, composed of melamine or a urethane/polyfunctional acrylic resin, a silicon type organic or inorganic film, and an inorganic film containing an antimony pentoxide type metal oxide.

The present invention will now be described in detail with reference to the following examples.

EXAMPLE 1

A three-neck flask having an inner volume of 1,000 ml was charged with 30 g of a compound represented by the following formula (P):

(P)

300 g of toluene, 500 g of 1N sodium hydroxide, 1 g of sodium borohydride and 100 mg of hydroquinone monomethyl ether, and 33 g of methacrylic acid chloride was gradually dropped into the mixture in nitrogen at 0° C. with stirring. Then, the mixture was stirred at 0° C. for 2 hours. Then, the toluene layer was washed and filtered, and the solvent was removed by distillation to obtain a compound represented by the following formula (Q):

(Q)

Figure 1:
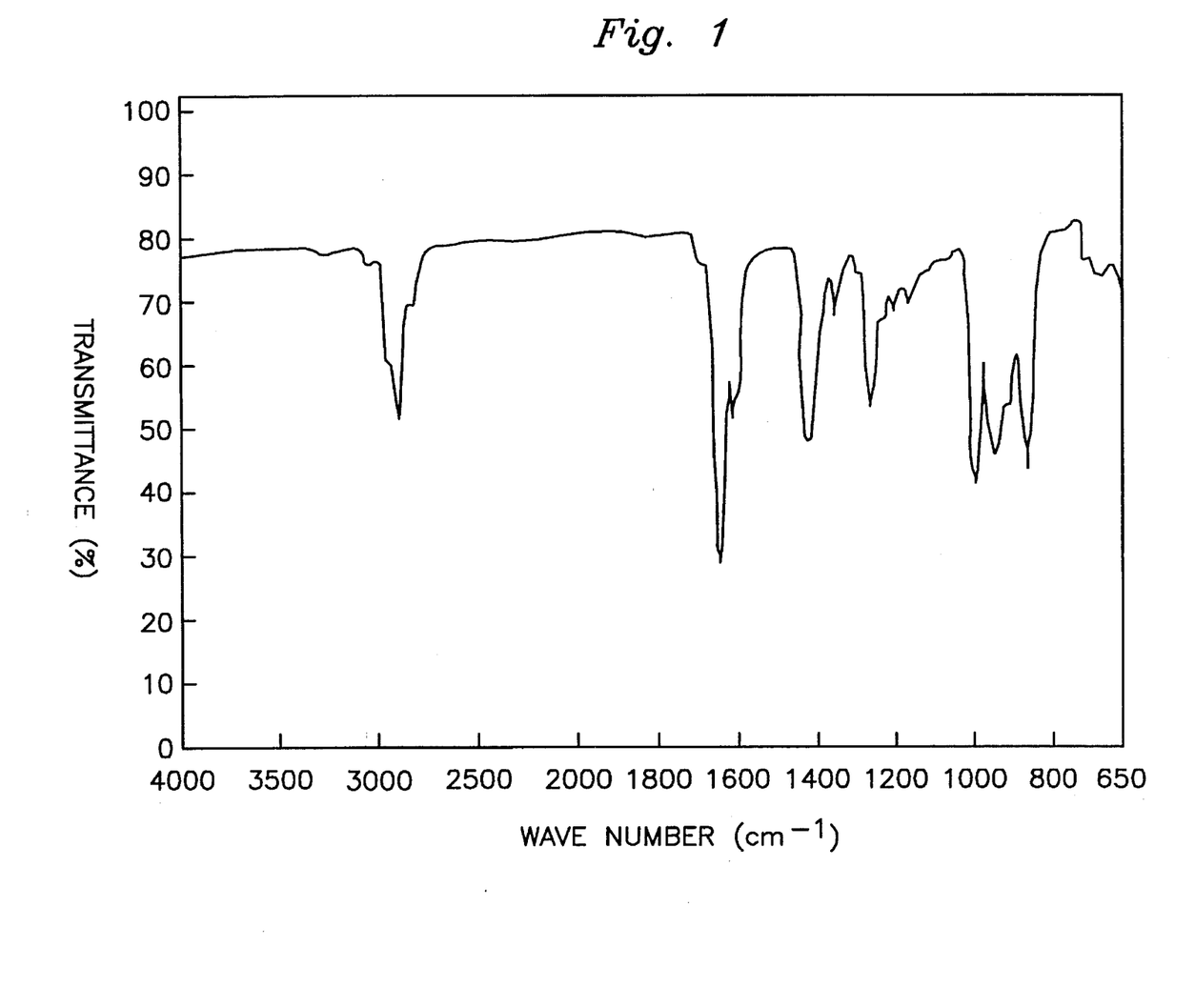
FIG. 1 is a chart of the infrared absorption spectrum of the compound of Example 1 of the present invention.

The appearance, refractive index and elementary analysis of this compound are shown in Table 1. The infrared absorption spectrum chart of this compound is shown in FIG. 1.

Since the absorption attributed to —S—CO— was observed at 1665 cm$^{-1}$, it was confirmed that the thiol (meth)acrylate represented by the formula (Q) was obtained.

The NMR results of the obtained compound were as shown below:

| | | |
|---|---|---|
| δ6.1 |  | 2H |
| δ5.6 | | 2H |
| δ2.8 | —CH$_2$—S—C—<br>‖<br>O | 4H |
| δ2.0 | | 6H |
| δ2.2 | —SCH$_3$ | 6H |
| δ3.1 | SCH$_3$<br>|<br>—CH— | 2H |

A solution comprising 99 parts by weight of the above compound and 1 part by weight of benzoyl peroxide was cast in a casting mold assembly composed of a glass mold and an adhesive tape, and the temperature was elevated from 50° C. to 120° C. over a period of 15 hours to obtain a resin. The properties of the obtained resin are shown in Table 2. When the infrared absorption spectrum was measured, the absorption attributed to CH$_2$=C< was not observed at 1620 cm$^{-1}$. Accordingly, it was confirmed that a thiol (meth)acrylate resin was obtained.

The heat resistance was evaluated based on the Shore D hardness at 100° C. The sample having a Shore D hardness of less than 50 was indicated by mark "C", the sample having a Shore D hardness of 50 to 70 was indicated by mark "B", and the sample having a Shore D hardness exceeding 70 and up to 100 was indicated by mark "A".

To examine generation of smell at processing, the sample was polished by a polishing machine and generation of smell was checked. The sample not generating any smell was indicated by mark "A", and other sample was represented by mark "C".

The refractive index was measured by a Pulfrich refractometer. The transmission and light resistance were measured by using a color computer and a fadeometer. The light resistance was evaluated after an exposure for 100 hours to a fadeometer, and the sample exhibiting a change in yellowness index (ΔYI) of less than 10 was indicated by mark "A", the sample exhibiting a ΔYI of 10 to 20 was indicated by mark "B", and the sample exhibiting a ΔYI of more than 20 was indicated by mark "C".

EXAMPLE 2

A compound represented by the following formula (R),

(R)

was prepared in the same manner as described in Example 1 except that acrylic acid chloride was used instead of methacrylic acid chloride. The properties of the obtained compound were determined in the same manner as described in Example 1. The results are shown in Table 1.

A resin was prepared from this compound in the same manner as described in Example 1. The properties of the obtained resin are shown in Table 2.

EXAMPLE 3

A compound represented by the following formula (T):

was prepared in the same manner as described in Example 1 except that a compound represented by the following formula (G):

was used instead of the compound of the formula (P).

Figure 2:
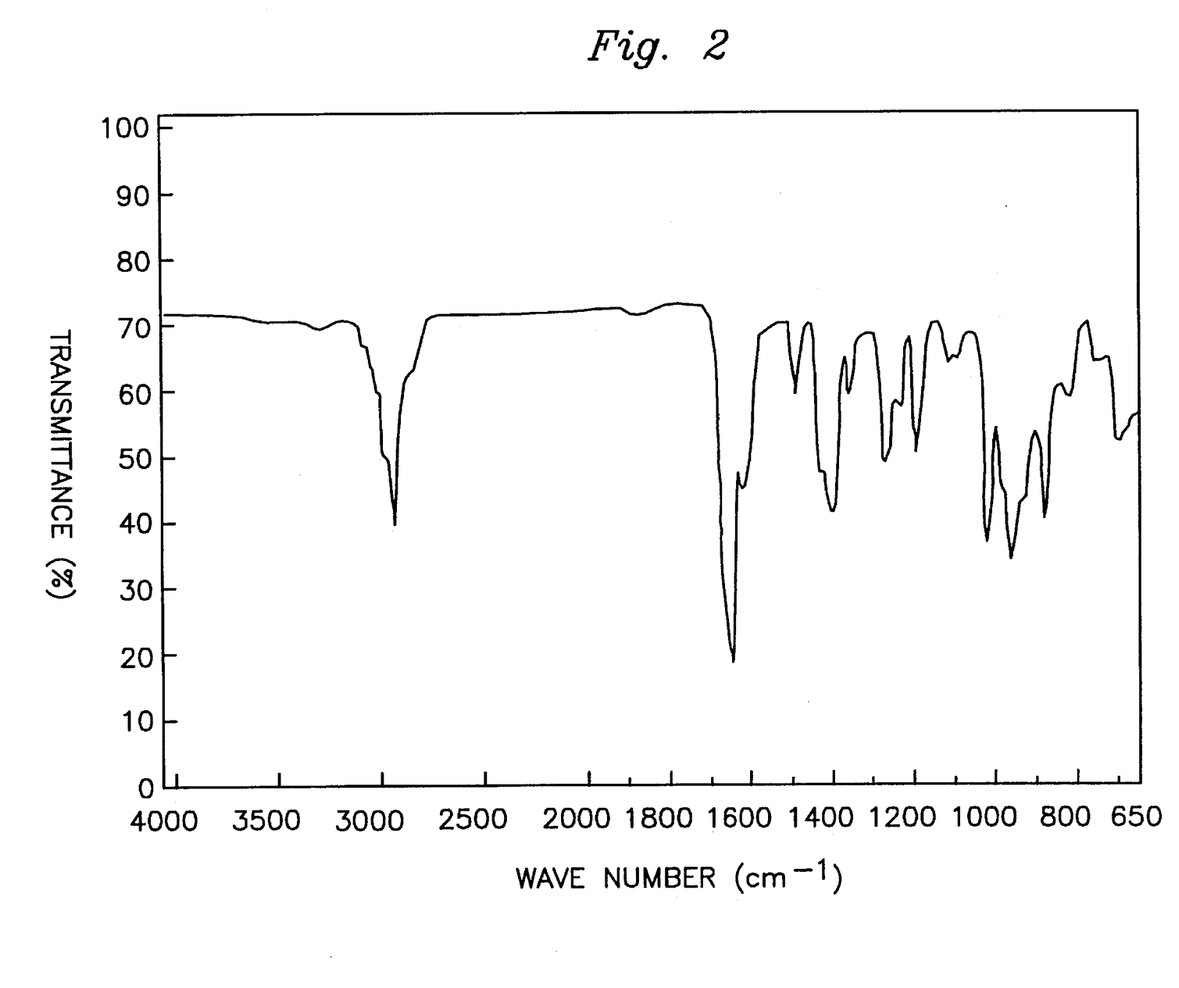
FIG. 2 is a chart of the infrared absorption spectrum of the compound of Example 3 of the present invention.

The infrared absorption spectrum of the obtained compound is six own in FIG. 2. Since the absorption attributed to —S—CO— was observed at 1665 cm$^{-1}$, it was confirmed that the compound of the formula (T) was obtained.

The NMR results of the above compound were as shown below:

| | | |
|---|---|---|
| δ6.1 | H\C=C/CH$_3$ / H \C— ‖ O | 2H |
| δ5.6 | H\C=C/CH$_3$ / H \C— ‖ O | 2H |
| δ2.0 | H\C=C/CH$_3$ / H \C— ‖ O | 6H |
| δ3.1 | —S—CH$_2$—CH$_2$—S—C— ‖ O | 4H |
| δ2.9 | —S—CH$_2$—CH$_2$—S—C— ‖ O | 4H |
| δ3.7 | —⟨phenyl⟩—CH$_2$—S— | 4H |
| δ7.4 | ⟨phenyl⟩ | 4H |

A resin was prepared from the obtained compound in the same manner as described in Example 1. The properties of the obtained resin are shown in Table 2. When the infrared absorption spectrum of the obtained resin was measured, the absorption attributed to CH$_2$=C< was not observed at 1620 cm$^{-1}$. Accordingly, it was confirmed that a thiol (meth)acrylate resin was obtained.

EXAMPLE 4

A compound represented by the following formula (S), was prepared in the same manner as described in Example 1 except that a compound represented by the following formula (M):

was used instead of the compound (P). The properties of the obtained compound were measured in the same manner as described in Example 1. The results are shown in Table 1.

A resin was prepared from the obtained compound in the same manner as described in Example 1. The properties of the obtained resin are shown in Table 2.

EXAMPLE 5

A compound represented by the following formula (U):

was prepared in the same manner as described in Example 1 except that a compound represented by the following formula (J):

was used instead of the compound of the formula (P). The properties of the obtained compound were measured in the same manner as described in Example 1. The results are shown in Table 1.

Figure 3:
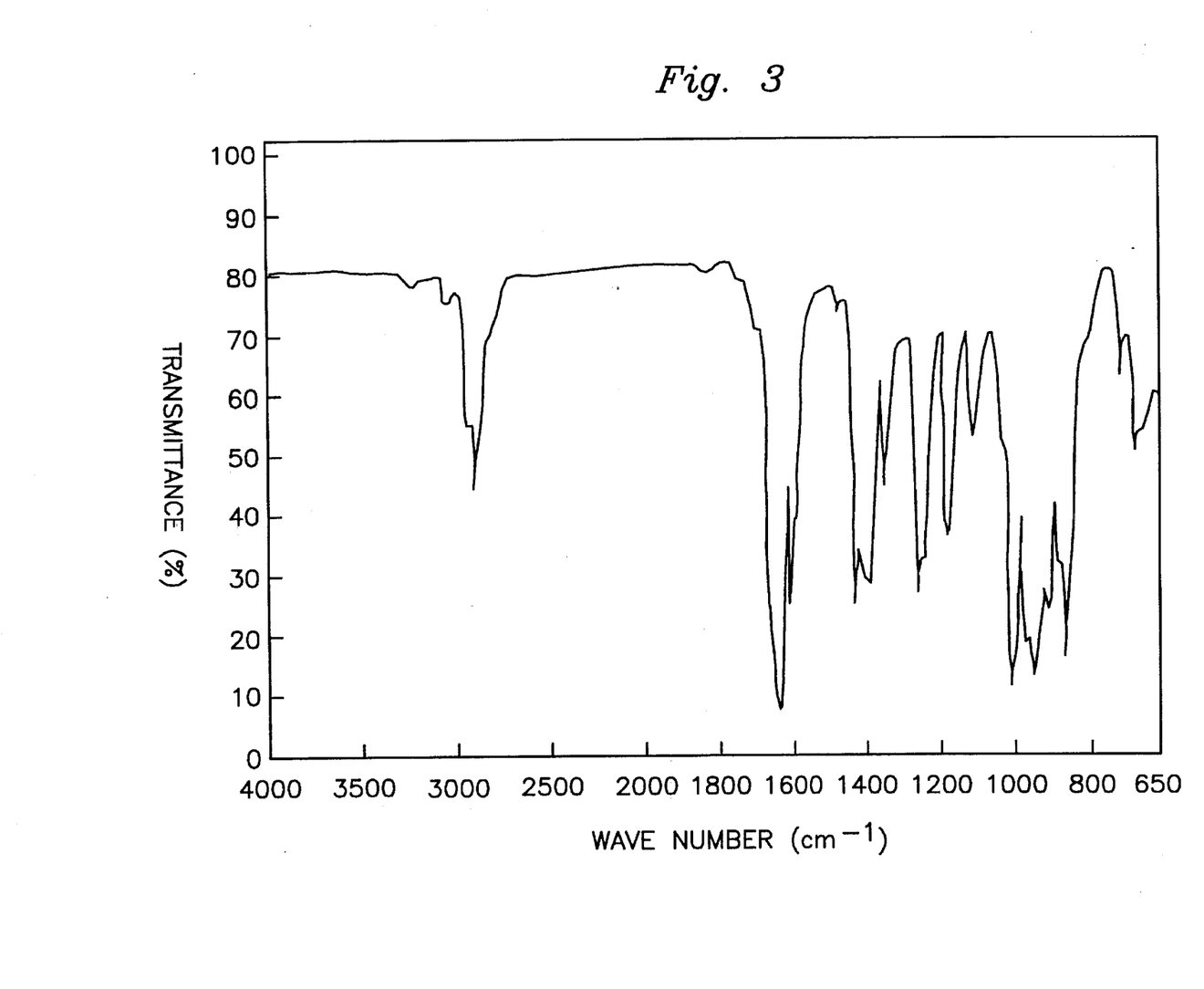
FIG. 3 is a chart of the infrared absorption spectrum of the compound of Example 5 of the present invention.

The infrared absorption spectrum of the obtained compound is shown in FIG. 3. Since the absorption attributed to —S—CO— was observed at 1665 cm$^{-1}$, it was confirmed that the thiol (meth)acrylate represented by the formula (U) was obtained.

The NMR results of the obtained compound were as shown below:

| | | |
|---|---|---|
| δ6.1 | H\C=C/CH$_3$ / H \C— ‖ O | 3H |

-continued

| δ5.6 | H\C=C/CH₃ , H/ \C(=O)— | 3H |
| δ3.2 | —SCH₂C<u>H</u>—CH₂—S—C—<br>　　　　\|　　\|　　　　\|\|<br>　　　　S—CH₂—　　　O | 1H |
| δ3.1 | —S—CH₂—C<u>H</u>₂—S—C—<br>　　　　　　　　　　　\|\|<br>　　　　　　　　　　　O | 6H |
| δ3.0 | —SC<u>H</u>₂—CH—C<u>H</u>₂—S—<br>　　　　　\|<br>　　　　　S—CH₂— | 4H |
| δ2.9 | —S—C<u>H</u>₂CH₂—S—C—<br>　　　　　　　　　　\|\|<br>　　　　　　　　　　O | 6H |
| δ2.0 | H\C=C/C<u>H</u>₃ , H/ \C(=O)— | 9H |

A resin was prepared from the compound of the formula (U) in the same manner as described in Example 1. The properties of the obtained resin are shown in Table 2. When the infrared absorption spectrum of the obtained resin was measured, the absorption attributed to CH₂=C< was not found at 1620 cm⁻. Accordingly, it was confirmed that a thiol (meth)acrylate resin was obtained.

EXAMPLE 6

A compound represented by the following formula (V):

was prepared in the same manner as described in Example 1 except that a compound represented by the following formula (O):

was used instead of the compound of the formula (P). The properties of the obtained compounds were measured in the same manner as described in Example 1. The results are shown in Table 1.

Then, 30 parts of the obtained compound of the formula (V) was mixed with 70 parts by weight of the compound of the formula (Q) obtained in Example 1, and a resin was prepared from this mixture in the same manner as described in Example 1. The properties of the obtained resin are shown in Table 2.

COMPARATIVE EXAMPLE 1

A three-neck flask having an inner volume of 1,000 ml was charged with 20 g of a compound represented by the following formula (α):

$$HSCH_2CH_2SCH_2CH_2SH \quad (\alpha)$$

300 g of toluene, 500 g of 1N sodium hydroxide, 1 g of sodium borohydride and 100 mg of hydroquinone monomethyl ether, and 33 g of methacrylic acid chloride was gradually dropped into the mixture in nitrogen at 0° C. with stirring and the mixture was stirred at 0° C. for 2 hours. Then, the toluene layer was washed and filtered, and the solvent was removed by distillation to obtain a compound represented by the following formula (β):

Then, 99 parts by weight of the obtained compound was polymerized in the same manner as described in Example 1 to obtain a resin. The properties of the obtained resin are shown in Table 2.

COMPARATIVE EXAMPLE 2

A compound represented by the following formula (δ):

was prepared in the same manner as described in Comparative Example 1 except that a compound represented by the following formula (γ):

was used instead of the compound of the formula (α).

The obtained compound was polymerized in the same manner as described in Example 1 to obtain a resin. The properties of the obtained resin are shown in Table 2.

COMPARATIVE EXAMPLE 3

A compound represented by the following formula (ξ), was prepared in the same manner as described in Comparative Example 1 except that a compound represented by the following formula (ε):

was used instead of the compound of the formula (α).

The obtained compound was polymerized in the same manner as described in Example 1 to obtain a resin. The properties of the obtained resin are shown in Table 2.

TABLE 1

| | Appearance | Refractive index | Elementary analysis (theoretical values) | Elementary analysis (found values) |
|---|---|---|---|---|
| Example 1 | Colorless transparent liquid | 1.58 | C:H:O:S 48.0:6.3:9.1:36.6 | C:H:O:S 48.5:6.5:9.0:35.8 |
| Example 2 | Colorless transparent liquid | 1.59 | C:H:O:S 44.7:5.6:9.9:39.8 | C:H:O:S 44.9:5.9:10.2:39.0 |
| Example 3 | Colorless transparent liquid | 1.62 | C:H:O:S 57.7:3.8:7.7:30.8 | C:H:O:S 57.6:3.6:7.8:31.0 |
| Example 4 | Colorless transparent liquid | 1.61 | C:H:O:S 61.9:6.3:6.3:25.4 | C:H:O:S 61.7:6.2:6.3:25.7 |
| Example 5 | Colorless transparent liquid | 1.59 | C:H:O:S 48.0:6.3:9.1:36.6 | C:H:O:S 47.8:6.2:8.9:37.1 |
| Example 6 | White transparent liquid | 1.64 | C:H:O:S 60.5:5.0:11.5:23.0 | C:H:O:S 60.3:4.9:11.9:22.8 |

TABLE 2

| | Heat resistance | Generation of smell at processing | Refractive index | Transmittance | Specific gravity | Light resistance | Abbe number | Casting temperature in mold (°C.) |
|---|---|---|---|---|---|---|---|---|
| Example 1 | A | A | 1.64 | 86 | 1.29 | A | 38 | 20 |
| Example 2 | A | A | 1.65 | 88 | 1.28 | A | 37 | 20 |
| Example 3 | A | A | 1.65 | 88 | 1.30 | A | 34 | 20 |
| Example 4 | A | A | 1.63 | 87 | 1.26 | A | 32 | 20 |
| Example 5 | A | A | 1.64 | 86 | 1.28 | A | 38 | 20 |
| Example 6 | A | A | 1.66 | 86 | 1.27 | B | 33 | 20 |
| Comp. Ex. 1 | B | C | 1.62 | 87 | 1.33 | A | 38 | 20 |
| Comp. Ex. 2 | A | A | 1.62 | 80 | 1.31 | C | 32 | 60 |
| Comp. Ex. 3 | A | A | 1.67 | 81 | 1.26 | C | 24 | 80 |

As shown above, the thiol (meth)acrylate of the present invention has a high refractive index, and a resin derived from this thiol (meth)acrylate has a high refractive index and generates little or no offensive smell of sulfur. Moreover, this resin has high transparency and an excellent heat resistance.

Therefore, the compound and resin of the present invention can be widely used in the fields of paints, electronic parts, and optical articles.

We claim:

1. A process for preparing a thiol methacrylate or acrylate resin consisting essentially of the steps:

incorporating 0.001 to 5 parts by weight of a radical polymerization initiator in 100 parts by weight of a thiol methacrylate or acrylate monomer represented by the following formula (1) or a monomer mixture comprising at least 10% by weight of the thiol methacrylate or acrylate monomer of the formula (1):

wherein $R^1$ represents a hydrogen atom or a methyl group and X represents a divalent group represented by the following formula (b):

and polymerizing the monomer or monomer mixture by irradiation with ultraviolet light.

2. The process according to claim 1 wherein said monomer mixture comprises at least 10% by weight of the thiol methacrylate or acrylate monomer of the formula (1) and up to 90% by weight of an olefinic compound.

3. A process for preparing a thiol methacrylate or acrylate resin consisting essentially of the steps:

incorporating 0.001 to 5 parts by weight of a peroxide radical polymerization initiator in 100 parts by weight of a thiol methacrylate or acrylate monomer represented by the following formula (1) or a monomer mixture comprising at least 10% by weight of the thiol methacrylate or acrylate monomer of the formula (1):

wherein $R^1$ represents a hydrogen atom or a methyl group and X represents a divalent group represented by the following formula (b):

and polymerizing the monomer or monomer mixture by irradiation with ultraviolet light.

4. The process defined in claim 1 wherein said monomer mixture comprises at least 15% by weight of the thiol methacrylate or acrylate monomer of formula (1).

5. The process defined in claim 1 wherein said monomer mixture comprises at least 30% by weight of the thiol methacrylate or acrylate monomer of formula (1).

6. The process defined in claim 1 wherein said monomer mixture comprises at least 60% by weight of the thiol methacrylate or acrylate monomer of formula (1).

7. The process defined in claim 1 wherein said monomer mixture comprises at least 70% by weight of the thiol methacrylate or acrylate monomer of formula (1).

8. The process defined in claim 1 wherein said monomer mixture comprises 15 to 90% by weight of the thiol methacrylate or acrylate monomer of formula (1) and 10 to 85 % by weight of a monomer having both a urethane bond and a methacrylate or acrylate group in the molecule.

9. The process defined in claim 8 wherein said monomer having both a urethane bond and a methacrylate or acrylate group in the molecule has a moiety represented by the following formula:

wherein Y represents an alkylene group having 1 to 10 carbon atoms, $R^4$ represents a hydrogen atom or a methyl group, and $l$ is an integer of 1 to 3.

* * * * *